United States Patent
Chu et al.

(10) Patent No.: US 11,839,677 B2
(45) Date of Patent: Dec. 12, 2023

(54) TOPICAL ANTIMICROBIAL COMPOSITION

(71) Applicant: Conopco, Inc., Englewood Cliffs, NJ (US)

(72) Inventors: Chung-Ching Chu, Shanghai (CN); Mingming Pu, Shanghai (CN); Zongxiu Wang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/926,284

(22) PCT Filed: Jun. 1, 2021

(86) PCT No.: PCT/EP2021/064590
§ 371 (c)(1),
(2) Date: Nov. 18, 2022

(87) PCT Pub. No.: WO2021/254773
PCT Pub. Date: Dec. 23, 2021

(65) Prior Publication Data
US 2023/0190607 A1    Jun. 22, 2023

(30) Foreign Application Priority Data

Jun. 19, 2020  (WO) ................ PCT/CN2020/097233
Jul. 21, 2020  (EP) ..................... 20186859

(51) Int. Cl.
*A61K 8/42*     (2006.01)
*A61K 8/49*     (2006.01)
*A61Q 5/00*     (2006.01)

(52) U.S. Cl.
CPC ............... *A61K 8/42* (2013.01); *A61K 8/498* (2013.01); *A61K 8/4926* (2013.01); *A61Q 5/006* (2013.01)

(58) Field of Classification Search
CPC ........ A61K 8/42; A61K 8/4926; A61K 8/498; A61Q 5/006
See application file for complete search history.

(56) References Cited

U.S. PATENT DOCUMENTS

2007/0298134 A1   12/2007  Iino et al.

FOREIGN PATENT DOCUMENTS

| CN | 102579308 | 7/2012 | | |
|---|---|---|---|---|
| CN | 102743694 | 10/2012 | | |
| CN | 105534820 | 5/2016 | | |
| CN | 105534820 A | * 5/2016 | ............... | A61K 8/97 |
| CN | 105726370 | 7/2016 | | |
| CN | 105769638 | 7/2016 | | |
| CN | 106420529 | 2/2017 | | |
| CN | 106726860 | 5/2017 | | |
| CN | 107126396 | 9/2017 | | |
| CN | 107137290 | 9/2017 | | |
| CN | 108658936 | 10/2018 | | |
| CN | 109303835 | 2/2019 | | |
| DE | 102011088957 | 6/2013 | | |
| JP | 6248297 | 9/1994 | | |
| JP | 2001288047 | 10/2001 | | |
| JP | 2002201192 | 7/2002 | | |
| JP | 2005206475 | 8/2005 | | |
| JP | 2010138130 | 6/2010 | | |
| JP | 2012012356 | 1/2012 | | |
| JP | 2017066145 | 4/2017 | | |
| JP | 2018024687 | 2/2018 | | |
| KR | 20100059301 | 6/2010 | | |
| WO | WO2004047789 | 6/2004 | | |
| WO | WO2006097192 | 9/2006 | | |
| WO | WO-2013092404 A2 | * 6/2013 | ........... | A61K 31/133 |
| WO | WO2018083675 | 5/2018 | | |

OTHER PUBLICATIONS

English machine translation of WO 2103/092404 A2 made May 16, 2023. (Year: 2023).*
English machine translation of CN 105534820 A made May 16, 2023. (Year: 2023).*
Wang et al., "Distribution survey, phytochemical and transcriptome analysis to identify candidate genes involved in biosynthesis of functional components in Zanthoxylum nitidum", Aug. 2020, Industrial Crops and Products, vol. 150, 112345, pp. 1-10. (Year: 2020).*
Search Report and Written Opinion in EP20186862.7; dated Jan. 12, 2021; European Patent Office (EPO).
Search Report and Written Opinion in PCT/EP2021/065328; dated Aug. 30, 2021; World Intellectual Property Org. (WIPO).
Search report and Written Opinion in PCT/EP2021/064590; dated Aug. 30, 2021; World Intellectual Property Org. (WIPO).
Search Report and Written Opinion in EP20186859.3; dated Jan. 12, 2021; European Patent Office (EPO).
Deshmukh, M.N., et al., "Two New Coumarins From Toddalia Aculeata", Phytochemistry, 15, pp. 1419-1420 (1976).
Hall, M. J., et al., "The fractional inhibitory concentration (FIC) index as a measure of synergy", Journal of Antimicrobial Chemotherapy, 11(5), pp. 427-433 (1983).
Randrianarivelojosia, M., et al., "Prenylated coumarins from Cedrelopsis longibracteata (Ptaeroxylaceae)", Biochemical Systematics and Ecology, 33(3), pp. 301-304 (2005).
Shen, Y.H., et al., "Coumarins from Coriaria nepalensis", Journal of Asian Natural Products Research, 8(4), pp. 345-350 (2006).

(Continued)

*Primary Examiner* — Michael B. Pallay
(74) *Attorney, Agent, or Firm* — Stephanie S. DelPonte

(57) ABSTRACT

Disclosed is a topical composition comprising: (i) an antimicrobial active which is at least one of piroctone, caprylhydroxamic acid, benzohydroxamic acid, or piroctone olamine; and (ii) norbraylin. Also disclosed is a non-therapeutic method of providing topical antimicrobial benefit on a topical surface of a human or animal body comprising a step of applying a safe and effective amount of the topical composition.

18 Claims, No Drawings

(56) References Cited

OTHER PUBLICATIONS

Wei, H., et al., "Studies on Chemical Constituents from the Root of Coriaria Npalensis Wall (Coriaria Sinica Maxim)", Acta Phamaceutica Sinica, 33(9), pp. 688-692 (1998).
Yao, G.D., et al., "Coumarins from the bark of Juglans mandshurica exhibited anti-hepatoma activities via inducing apoptosis", Journal of Asian Natural Products Research, 19(11), pp. 1134-1142 (2017).
Rahmani, M., et al., "Constituents of Acronychia Laurifolia", Fitoterapia, 67(2), p. 180 (1996).
Database WPI, Week 201770, XP002801459, cited in European Search Report dated Jan. 12, 2021 (4 pages).
Database WPI, Week 2019738, XP002801460, cited in European Search Report dated Jan. 12, 2021 (2 pages).
Database WPI, Week 200265, XP002801465, cited in European Search Report dated Jan. 12, 2021 (2 pages).
Database WPI, Week 201880, XP002801466, cited in European Search Report dated Jan. 12, 2021 (2 pages).
Co-pending Application, U.S. Appl. No. 17/926,267, filed Nov. 18 2022.

* cited by examiner

TOPICAL ANTIMICROBIAL COMPOSITION

FIELD OF THE INVENTION

This invention relates to topical antimicrobial compositions, especially cosmetic compositions and more particularly to cosmetic compositions comprising actives that interact to provide synergistic antimicrobial effect and useful at least against some microbes associated with conditions of cosmetic relevance such as dandruff and acne.

BACKGROUND OF THE INVENTION

The invention relates to an antimicrobial composition useful for cleaning and/or care of any body part but especially suitable for hair, and scalp care, hand hygiene or for facial care and cleansing.

Dandruff is an issue that affects many people globally. The condition is manifested by the shedding of clumps of dead skin cells from the scalp. These are white and readily visible therefore they present an aesthetically displeasing appearance. A factor that contributes to dandruff is certain members of the Malassezia yeasts. To combat them, various antidandruff compositions such as shampoos are available. Usually such shampoos contain surfactants and one or more anti-dandruff agent. Typical antidandruff agents are metal pyrithione e.g., zinc pyrithione (ZPTO), octopirox (piroctone olamine), azole antimicrobials (e.g. climbazole), selenium sulfide and combinations thereof.

While the problem of dandruff is mitigated to a large extent through use of the above actives in such shampoos, there is a need for more efficacious compositions.

Acne, also known as Acne vulgaris, is a common skin condition that affects nearly all adolescents and adults. It has a complex etiology involving abnormal keratinization and excess sebum production. Acne usually occurs in areas rich in sebaceous glands like the face, neck and back. A bacterium *Cutibacterium acnes* (*C. acnes,* formerly known as *Propionibacterium acnes* or *P. acnes*) has also been implicated in occurrence of acne. Acne has been treated in many ways. Most treatments take several weeks to months before a noticeable change is seen. Benzoyl peroxide which has an antibacterial effect has been used for mild cases of acne and is also believed to prevent formation of further acne. In very severe cases of acne, antibiotics like tetracycline, erythromycin and clindamycin have been used.

It is thus an object of the present invention to provide for a topical composition that exhibits synergistic antimicrobial activity as compared to the individual components.

SUMMARY OF THE INVENTION

We have determined that when a certain active which is usually found in the natural plants is formulated together with a typical antimicrobial active which is at least one of piroctone, caprylhydroxamic acid, benzohydroxamic acid, or piroctone olamine, the combination is highly efficacious against some microbes associated with conditions like dandruff and acne. That led us to the inference that compositions comprising the abovementioned combination could have antidandruff, antiacne and general antimicrobial activity and could be suitable for use in e.g., shampoo, body and face care. The certain active referred to hereinabove is norbraylin.

Therefore, in accordance with a first aspect is disclosed a topical composition comprising:

(i) an antimicrobial active which is at least one of piroctone, caprylhydroxamic acid, benzohydroxamic acid, or piroctone olamine; and
(ii) norbraylin.

In accordance with a second aspect is disclosed a non-therapeutic method of providing topical antimicrobial benefit on a topical surface of a human or animal body comprising a step of applying a safe and effective amount of a topical antimicrobial composition of the first aspect.

In accordance with a third aspect is disclosed a composition of the first aspect for use in providing antimicrobial benefit on a topical surface of a human or animal body.

DETAILED DESCRIPTION OF THE INVENTION

The compositions according to the present invention comprise a topically acceptable carrier, vehicle or diluent which can have a variety of different forms. The topically acceptable carrier should preferably be non-irritant. "Topically-acceptable" therefore means that the carrier is suitable for topical application to the skin without causing any untoward safety or toxicity concerns. In other words, these carriers are suitable for use on mammalian skin. The typical carrier can be in the form of a hydro-alcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light cream and heavy creams. The emulsions can also include microemulsion systems. Other suitable topical carriers include anhydrous solids and semisolids (such as gels and sticks); and aqueous based mousse systems. Nonlimiting examples of the topical carrier systems useful in the present invention are described hereinafter.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of or "composed of." In other words, the listed steps or options need not be exhaustive. It is noted that the examples given in the description below are intended to clarify the invention and are not intended to limit the invention to those examples per se. Similarly, all percentages and ratios contained herein are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated. The various features of the present invention referred to in individual sections above apply, as appropriate, to other sections mutatis mutandis. Consequently, features specified in one section may be combined with features specified in other sections as appropriate. Any section headings are added for convenience only and are not intended to limit the disclosure in any way.

By a topical composition is meant a composition for external application in the form of a leave-on or wash-off format meant for cleaning or disinfecting topical areas e.g. skin and/or hair and or oral cavity of mammals, especially humans. Such a composition includes any product applied to a human body for also improving appearance, cleansing, odor control or general aesthetics. In accordance with one aspect, the compositions in accordance with the invention are rinse off compositions. Alternatively, they are leave-on compositions. The compositions of the present invention could be in the form of a liquid, lotion, cream, foam or gel, or toner, or applied with an implement or via a face mask, pad or patch. "Skin" as used herein is meant to include skin on the face and body (e.g., neck, chest, back, arms, underarms, hands, legs, buttocks and scalp). The composition of the invention is also of relevance to applications on any other external substrates of the human body other than skin e.g. hair.

By 'an antimicrobial composition' as used herein, is meant to include a composition for topical application to skin, hair and/or scalp of mammals, especially humans. Such a composition is generally applied on to the desired topical surface of the body for few seconds to up to 24 hours. When the time of application is low say of the order of a few seconds to a few minutes after which the composition is rinsed off with water or wiped away, such a composition is known as a cleansing composition or a rinse-off composition. When the composition is applied for longer time say from several minutes to up to 24 hours and washed off usually during the process of normal personal cleaning, such a composition is known as a leave-on composition. It is more preferably used for preventing or alleviating the symptoms of dandruff on the scalp and/or hair, for antiacne benefit, or for disinfecting the hand or other parts of the human body.

"Hair care composition" as used herein, is meant to Include a composition tor topical application to hair. Non-limiting examples of such compositions include leave-on hair lotions, creams, arid wash-off shampoos, conditioners, shower gels, or a toilet bar. When the composition of the invention is a hair care composition, it preferably is a wash-off composition, especially shampoo or a conditioner.

The invention relates to a topical composition comprising:
(i) an antimicrobial active which is at least one of piroctone, caprylhydroxamic acid, benzohydroxamic acid, or piroctone olamine; and
(ii) norbraylin.

Hydroxamic Acids and Hydroxamic Acid Derivatives

A hydroxamic acid is a class of organic compounds bearing the functional group RC(O)N(OH)R', with R and R' as organic residues and CO as a carbonyl group.

The antimicrobial active in accordance with the invention is at least one of hydroxamic acids or hydroxamic acid derivatives. The hydroxamic acid is piroctone, caprylhydroxamic acid, or benzohydroxamic acid, more preferably it is caprylhydroxamic acid. The hydroxamic acid derivative is piroctone olamine.

The antimicrobial active according to present invention is at least one of piroctone, caprylhydroxamic acid, benzohydroxamic acid or piroctone olamine. It is more preferred that the antimicrobial active according to present invention is at least one of caprylhydroxamic acid or piroctone olamine. It is most preferred that the antimicrobial active is piroctone olamine.

Piroctone is a cyclic hydroxamic acid that consists of 1-hydroxypyridin-2-one bearing methyl and 2,4,4-trimethylpentyl substituents at positions 4 and 6 respectively. The CAS number is 50650-76-5 and the compound has the general formula (a) as below:

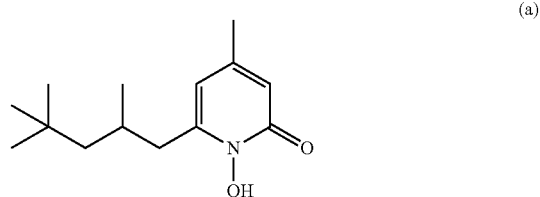

(a)

Caprylhydroxamic acid is an amino acid derived from coconut oil. It is a preservative and broad spectrum antifungal agent. The CAS number is 7377-03-9 and the compound has the general formula (b) as below:

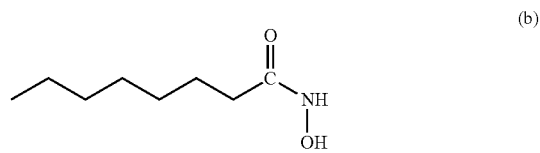

(b)

Benzohydroxamic acid is one of hydroxamic acids. The CAS number is 495-18-1 and the compound has the general formula (c) as below:

(c)

Piroctone Olamine is an olamine salt of the hydroxamic acid derivative piroctone which is a typical antimicrobial active. It is commonly known as piroctone ethanolamine with the trade name Octopirox®.

The piroctone olamine according to the present invention is a 1:1 compound of 1-hydroxy-4-methyl-6-(2,4,4-trimethylpentyl)-2(1H)-pyridinone with 2-aminoethanol and is also designated 1-hydroxy-4-methyl-6-(2,4,4-trimethylpentyl)-2 (1H) pyridinone monoethanolamine salt. The CAS number is 68890-66-4 and the compound has the general formula (d) as below:

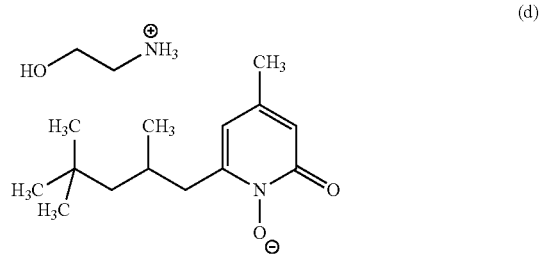

(d)

Amount of the antimicrobial active which is at least one of hydroxamic acids or hydroxamic acid derivatives in the composition of the invention would depend on the type of the topical composition and the precise nature of other antimicrobial actives used. It is preferred that the composition comprises 0.01 to 10 wt % of said antimicrobial active, more preferably 0.1 to 5 wt %, furthermore preferably 0.5 to 3 wt % by weight of the composition.

Norbraylin

Norbraylin according to the present invention is 6-Hydroxy-8,8-dimethylpyrano[2,3-f]chromen-2-one ($C_{14}H_{12}O_4$). The CAS number is 60796-64-7 and the compound has the general formula (e) as below:

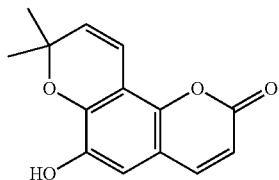

(e)

Such norbraylin could also be found in plants—*Zanthoxylum nitidum*, *Toddalia asiatica*, and *Cedrelopsis grevei*.

It is preferred that the amount of the norbraylin in the compositions of the invention is from 0.01 to 10 wt %. More preferably the amount is 0.01 to 5% by weight of the composition and most preferably 0.1 to 2%.

Preferably the composition of the invention comprises extract of *Zanthoxylum nitidum*, alternatively extract of *Toddalia asiatica* or *Cedrelopsis grevei*, which in turn comprises said norbraylin. A measured amount of the extract is chosen so that the requisite amount of the norbraylin contained therein get included in the composition.

*Zanthoxylum nitidum* extracts containing norbraylin are commercially available from a variety of different sources. For example, an extract of *Zanthoxylum nitidum*, is available from Dalian Institute of Chemical Physics, Chinese Academy of Sciences. Alternatively, a person of ordinary skill in the art would be able to isolate by using any suitable isolation and purification method known in the art. In some embodiments, the extract of *Zanthoxylum nitidum* may be obtained from dried *Zanthoxylum nitidum* plant and can be prepared by any means known or to be developed in the art.

Usually, plant extracts can be prepared using aqueous solvents including water and alcohol, or using supercritical carbon dioxide, that works to draw out beneficial plant components. For example, the herb raw material is crushed into small pieces and soaked in 10-fold volume of deionized water for 30 min, then reflux extracted for 30 min for twice. After filtration, the liquid can be dried to obtain the extract powder. Alternatively, the herb raw material is crushed into small pieces and soaked in 10-fold volume of 95% ethanol for 24 hours for twice. The two filtration solutions were combined and filtered. The solvent in the supernatant were removed by evaporation to obtain the extract powder.

As the compositions comprise antimicrobial active and norbraylin, it is preferred that a ratio is maintained between the amount of the active ingredients to get optimal efficacy. Preferably the weight ratio of the amount of said norbraylin to said antimicrobial active is from 1:10 to 100:1, more preferably from 1:2 to 50:1, furthermore preferably from 1:1 to 20:1, particularly preferably from 3:1 to 10:1, most preferably from 5:1 to 10:1.

The sum of the fractional inhibitory concentrations (ΣFIC) is widely used in the context of combinations of antimicrobial ingredients. It is a tool to determine whether the antimicrobial ingredients (when used in combination) have synergistic effect or antagonistic effect or neither of the two, i.e., an additive effect. The present inventors have resorted to the ΣFIC test to evaluate the combined effect of antimicrobial active with norbraylin against *M. furfur*.

It is believed that while the antimicrobial active and norbraylin according to the present invention present in the compositions of the invention, the norbraylin compound interacts synergistically with the antimicrobial active to make it even more efficacious.

It is preferred that the topical composition of the invention comprises piroctone olamine and norbraylin. In this case it is preferred that weight ratio of the amount of norbraylin to that of piroctone olamine is 1:10 to 100:1, alternatively 1:2 to 50:1 and further alternatively 1:1 to 10:1.

It is preferred that the topical composition of the invention comprises caprylhydroxamic acid and norbraylin. In this case it is preferred that weight ratio of the amount of norbraylin to that of caprylhydroxamic acid is 1:10 to 100:1, alternatively 1:2 to 50:1 and further alternatively 1:1 to 10:1.

Other Ingredients

The composition of the invention preferably comprises a cosmetically acceptable vehicle. The cosmetically acceptable vehicle is such that the composition can be prepared, e.g., as a shampoo, conditioner, body wash, hand wash or face wash product, cream, lotion, gel, powder, ointment, hand sanitiser or a soap bar and the rest of the ingredients would vary accordingly.

In one aspect the topical compositions in accordance with the invention is a hair care composition. Preferably such a composition is a shampoo, a hair conditioner, a hair serum or a hair oil. Most preferably the topical composition is an antidandruff composition effective against at least some *Malessezia* spp.

When the composition of the invention is a shampoo, it preferably comprises other ingredients which are generally included in such compositions.

A shampoo preferably comprises 1 to 20 wt %, more preferably 2 to 16 wt %, furthermore preferably from 3 to 16 wt % anionic surfactants, e.g. an alkyl sulphate and/or ethoxylated alkyl sulfate surfactant. Preferred alkyl sulfates are 08-18 alkyl sulfates, more preferably $C_{12-18}$ alkyl sulfates, preferably in the form of a salt with a solubilising cation such as sodium, potassium, ammonium or substituted ammonium.

Particulartly preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair. Examples include the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typically, suitable anionic surfactants include sodium ( )eyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate. Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable. The shampoo composition of the invention preferably additionally comprises 0.1 to 10 wt %, more preferably from 0.5 to 8 wt % of an amphoteric surfactant, preferably a betaine surfactant such as alkyl amidopropyl betaine surfactant, for example cocoamidopropyl betaine.

The pH of the composition is preferably equal to or higher than 4.0, more preferably in the range of 5.0 to 10.0.

It is preferred that the shampoo composition additionally comprises 0.1 to 3 wt %, more preferably 0.1 to 1.5 wt % of a zinc compound. The presence of zinc in the composition is believed to improve the antidandruff efficacy. Suitable zinc compounds are ZPTO, zinc oxide, zinc citrate, zinc malonate, zinc carbonate or a combination thereof.

Preferably the shampoo composition additionally comprises 0.01 to 2 wt %, more preferably 0.025 to 0.75 wt % conazole fungicide. Preferably the conazole fungicide is ketoconazole or climbazole or mixture thereof. The presence of a conazole fungicide is believed to improve the deposition of zinc pyrithione (ZPTO).

The shampoo composition further preferably comprises a suspending agent. Suitable suspending agents are polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol distearate are preferred long chain acyl derivatives, since these impart pearlescence to the composition. Polyacrylic acid is available commercially as Carbopol® 420, Carbopol® 488 or Carbopol® 493. Polymers of acrylic acid cross-linked with a polyfunctional agent may also be used; they are available commercially as Carbopol® 910, Carbopol® 934, Carbopol® 941 and Carbopol® 980. An example of a suitable copolymer of a carboxylic acid containing monomer and acrylic acid esters is Carbopol® 1342. All Carbopol (trademark) materials are available from Goodrich.

Suitable cross-linked polymers of acrylic acid and acrylate esters are Pemulen® TR1 and Pemulen® TR2. A suitable hetero polysaccharide gum is xanthan gum, for example that available as Kelzan.

Mixtures of any of the above suspending agents may be used. Preferred is a mixture of cross-linked polymer of acrylic acid and crystalline long chain acyl derivative.

Suspending agent, if included, will generally be present at 0.1 to 10 wt %, preferably from 0.5 to 6 wt %.

A composition of the invention may contain other ingredients for enhancing performance and/or consumer acceptability. Such ingredients include fragrance, dyes and pigments, pH adjusting agents, pearlisers or opacifiers, viscosity modifiers, preservatives, and natural hair nutrients such as botanicals, fruit extracts, sugar derivatives and amino acids.

It is preferred that the shampoo composition is aqueous based. It preferably comprises 70 to 95 wt % water.

Hair Conditioner

As an alternative, the topical composition of the invention is a hair conditioner. When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone, preferably a non-volatile silicone. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

It is preferred that hair conditioner composition of the invention comprises 0.1 to 10 wt %, more preferably from about 0.1 to about 8 wt % silicone. Alternatively, the hair conditioner is silicone-free, containing not more than 1 wt % silicone. It is preferred that pH of the composition is more than 4.0, more preferably 5.0 to 7.0.

Hair conditioner composition of the invention preferably may also comprise 0.5 to 10 wt % fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

Skin Cleansing

The composition of the invention may be used for skin care e.g. body or face wash. The topical composition may further comprise a surfactant. The preferred surfactants are nonionic surfactants.

Thus, in a highly preferred aspect, the topical compositions include the surfactant selected from the group of anionic surfactants.

When the surfactants are present, the topical composition preferably comprises 1 to 90% surfactant by weight of the composition.

When surfactant is used, a particularly preferred surfactant is soap. Soap is a suitable surfactant for personal washing applications of the topical composition of the invention. When present, the soap, of the present is preferably present in an amount of 1 to 90%, preferably from 10 to 85%, more preferably 25 to 75% by weight of the composition. Preferred compositions may include other known ingredients such as perfumes, pigments, preservatives, emollients, sunscreens, emulsifiers, gelling agents and thickening agents. Choice of these ingredients will largely depend on the format of the composition.

Water is a preferred carrier. When water is present, it is preferably present in at least 1%, more preferably at least 2%, furthermore preferably at least 5% by weight of the composition. When water is the carrier, a preferred liquid composition comprises 10 to 99.8% by weight water. The liquid topical composition is useful as a skin antiseptic liquid, for skin cleansing, in particular for hand wash or a face wash. When water is the carrier, a preferred solid composition comprises 5 to 30% by weight water.

The solid topical composition is preferably in form of a shaped solid, more preferably a bar. The solid topical composition is particularly useful for skin cleansing in particular for hand wash or a face wash.

According to another aspect, inorganic particulate material is also a suitable carrier. When inorganic particulate material is the carrier, the topical composition is in a solid form. Preferably the inorganic particulate material is talc. When the inorganic particulate material is talc, the solid antimicrobial composition is particularly useful as a talcum powder for application on face or body.

In another aspect of the present invention, the composition of the present invention is suitable for use in wipes for personal hygiene.

Use and Method in Accordance with the Invention

In accordance with a second aspect is disclosed a topical composition of the first aspect for use in providing antimicrobial benefit on a topical surface of a human or animal body. It also discloses a topical composition for use against at least some *Malessezia* spp on a topical surface of a human or animal body. Preferably the topical composition is an antidandruff composition effective against at least some *Malessezia* spp on a topical surface of a human or animal body. Alternatively the topical composition is an antiacne composition effective at least against *C. acnes*. Further alternatively the topical composition is rinse-off or a leave-on composition effective at least against *S. aureus*. It is preferred that the use in accordance with the invention is for non-therapeutic purpose. Preferably the non-therapeutic purpose means for cosmetic purposes. Alternatively, the use of the compositions in accordance with the invention is for therapeutic purpose. Persons ordinarily skilled in the art understand the difference between therapeutic and non-therapeutic uses of the compositions.

In accordance with another aspect is disclosed a non-therapeutic method of providing topical antimicrobial benefit on a topical surface of a human or animal body comprising a step of applying a safe and effective amount of a topical composition of the first aspect. The term safe an effective amount is well known to persons skilled in the art and such amounts may vary depending on the product format, for example, the said amount in the case of a leave on composition could be 1 to 2 ml for each application, while the same amount could be 5 to 10 ml for each application in the case of shampoos. The method may be utilized for preventing or treating acne, dandruff or for maintaining general hygiene.

Preferaly the topical composition is an antidandruff composition effective against at least some *Malessezia* spp. Alternatively, the topical composition is an antiacne composition effective at least against *C. acnes*. Further alternatively the topical composition is rinse-off or a leave-on composition effective at least against *S. aureus*. The method is more effective when the weight ratio of the norbraylin to the antimicrobial active on the *Malassezia furfur* cell is in the range of 1:10 to 100:1, even more effective when in the range of 3:1 to 100:1.

In accordance with another aspect is disclosed a composition for use in providing antimicrobial benefit on a topical surface of a human or animal body.

In accordance with another aspect is disclosed a topical composition for use as an antidandruff composition effective against at least some *Malessezia* spp. In accordance with yet another aspect is disclosed a topical composition for use as an antiacne composition effective at least against *C. acnes*. In accordance with yet another aspect is disclosed a rinse-off or a leave-on composition effective at least against *S. aureus*.

The invention will now be described in detail with the help of the following non-limiting examples.

EXAMPLES

Example 1

The antimicrobial efficacy of exemplary compositions according to the invention was determined as against *M. furfur*.

The concerned procedures will now be briefly explained.

Method 1: ΣFIC Assay Against *M. furfur*.

Step 1: Microbe Culture and Preparation

*M. furfur* (CBS1878) was maintained on MD agar plate (Solution A) was cultured into 20 ml of growth medium Pityrosporum Broth (PB, Solution B). They are then incubated at 32° C. for 48 hours with shaking. Then, 1 ml of the first broth culture is transferred into 9 ml of fresh PB and incubated at 32° C. for 48 hours with shaking. The final culture should contain 2 to $6 \times 10^6$ cells/ml. This is achieved by diluting using PB to $5 \times 10^5$ cells/ml.

Preparation of Solution A:

| Modified Dixon Agar (MD) | |
|---|---|
| 36 g | Malt Extract (Oxoid) |
| 6 g | Mycological Peptone (Oxoid) |
| 10 | Purified Agar (Oxoid) |
| 20 g | Ox-bile (Oxoid) |
| 2 ml | Oleic acid (Sigma) |
| 2 ml | Glycerol (Sigma) |
| 10 ml | Tween 40 (Sigma) |
| Deionized Water to 1000 ml | |
| 50 mg (1 vial) dissolved in 2 ml 95% ethanol | |
| Chloramphenicol (Oxoid SRO78E) | |
| (Ensure stirring thoroughly including after autoclaving) | |

Preparation of Solution B:

| Pityrosporum Broth (PB) | |
|---|---|
| 10 g | Bacteriological Peptone |
| 0.1 g | Yeast extract |
| 10 g | Ox-bile |

-continued

| Pityrosporum Broth (PB) | |
|---|---|
| 2.5 g | Taurocholic acid |
| 10 g | Glucose |
| 1 L | Deionised water |
| 0.5 ml | Tween60 |
| 1 ml | Glycerol |
| | Adjusted pH to 6.2 |
| | After sterilization |
| 0.5 ml | UHT milk |

Step 2: In-Vitro Susceptibility Testing

Octopirox® was serially diluted (2-fold) to prepare in a range of 60-1000 ppm in the growth medium. Testing norbraylin (stock: 10 mg/ml) was 2-fold serially diluted in DMSO to prepare in a range of 5000-5 ppm. Binary combinations of Octopirox® and the testing compound were prepared in 96-well plate by mixing 10 µl of Octopirox® solution with 10 µl of testing compound. The solution in each well were further mixed with 180 µl of M. furfur strain suspensions in PB.

The final cell density in the testing plate is around $5*10^4$ cell/ml. The final concentration of each ingredient in ppm (parts per million) after (20-fold dilution) was as follows. Each of these concentrations was tried out to determine the FIC value for (either of) Octopirox® in combination with norbraylin. The broth medium and solvent control as taken as negative controls for comparison of results.

Octopirox®—6.25, 3.125 and 0 ppm.

Norbraylin—500, 250, 125, 62.5, 31.25, 15.63, 7.8, 3.9, 2.0, 1.0, 0.5 and 0 ppm

Multi-channel pipette was used to mix the compound and strain suspension. Thereafter the 96-well plates were incubated in an incubator. OD600 (start) will be read. For M. furfur, after 2-days incubation, OD600 (end) will be read. Thereafter alamar blue (10%) was added and incubated for 8 h. Finally, the change in colour of the indicator was monitored to check for visible signs of microbial growth or inhibition of the growth. If the color changed to red it indicated growth (of microbes) and blue indicated no growth or inhibition of growth.

Step 3: Calculation: ΣFIC Test (1) Minimum Inhibition Concentration (MIC):

The MIC is defined as the absolute lowest concentration of active that provides complete microbial growth inhibition as indicated by the blue color of alamar blue under the tested condition.

(2) Fractional Inhibition Concentration (FIC):

The ΣFIC test was conducted based on the principle previously described in Hall M J, Middleton R F, & Westmacott D (1983), The fractional inhibitory concentration (FIC) index as a measure of synergy. Journal of Antimicrobial Chemotherapy 11(5):427-433. The procedure is as follows:

The differing behaviours of inhibitory antimicrobials in isolation and mixtures have been widely explored using the concept of the Fractional Concentration (FC) and Fractional Inhibitory Concentration (FIC). The parameter can be defined as follows:

$$FIC\ (\text{component } a) = \frac{MIC\ (\text{component } a \text{ tested in the mixture})}{MIC\ (\text{component } a \text{ tested as a single active})}$$

(3) Synergy and Additivity

The interactions between antimicrobials can be additive, synergistic or antagonistic depending on whether the efficacy of the combination is equivalent to, greater than or less than that obtained for the same total concentration of the individual components when tested alone.

After all the observations were recorded and tabulated, the Fractional Inhibition Concentration (FIC) was calculated.

The combination effect of inhibitory antimicrobials is widely explored using the concept of the Fractional Concentration (FC) and Fractional Inhibitory Concentration (FIC). This parameter is defined as follows:

ΣFIC=FIC (component 1)+FIC (component 2)

Further, the inference that could be drawn from the value of ΣFIC is summarised in the table below. There is no consistent approach in the academic or patent literature in defining precise limiting ΣFIC values that differentiate synergy from additivity or antagonism. In this study, we have adopted a liberal approach defining any binary mixture with ΣFIC<0.9 as showing evidence of synergistic behavior.

| ΣFIC = 1 | additive antimicrobial activity | not acceptable |
|---|---|---|
| ΣFIC > 1 | antagonistic antimicrobial activity | not acceptable |
| ΣFIC < 0.9 | synergistic antimicrobial activity | inventive |

The final concentration of each ingredient in ppm (parts per million) after (10-fold dilution) was as follows. Each of these concentrations was tried out to determine the FIC value for (either of) Octopirox® in combination with norbraylin.

Results:

It was observed that there was synergistic effect of Octopirox® with norbraylin against M. furfur (Table 1).

TABLE 1

Effect of Octopirox ® and norbravlin against M. furfur

| Example | Combination | ΣFIC |
|---|---|---|
| 1 | Octopirox ® + Norbraylin | 0.75 |

The observation tabulated in Tables 1 clearly indicates that norbraylin interacts synergistically with Octopirox® (the antimicrobial active according to the present invention). The synergistic interaction was evident from the fact that the ΣFIC was less than 0.9.

Combination of Octopirox® with Other Known Antimicrobial Active ZPTO as Negative Control.

Invitro ΣFIC assay against M. furfur similar to that used above was used to carry out experiments to determine if the interaction between Octopirox® and other well-known antimicrobial active like zinc pyrithione yields synergistic antimicrobial activity. The experiments were carried out over a concentration range of ingredients as below:

Octopirox®—50, 25, 12.5, 6, 3 and 0.

ZnPT: 50, 25, 12.5, 6.25, 3.13, 1.56, 0.78, 0.39, 0.2, 0.1, 0.05 and 0.

The ΣFIC assay was carried out and the data indicates that the Octopirox® cannot interact synergistically with ZPTO to yield synergistic antimicrobial activity. Thus, one cannot conclude that combinations of piroctone olamine with any known antimicrobial active will always yield synergies.

Surprisingly, the combination of norbraylin with the antimicrobial active claimed in the present invention displays synergistic behaviour.

Example 2

The antimicrobial efficacy of exemplary compositions according to the invention was determined as against *M. furfur*.

Microorganism Preparation:

*M. furfur* (CBS 1878) was maintained on MD agar plate (Solution A) was cultured into 20 ml of growth medium Pityrosporum Broth (PB, Solution B).

They are then incubated at 32° C. for 48 hrs with shaking. Then, 1 ml of the first broth culture is transferred into 9 ml of fresh PB and incubated at 32° C. for 48 hrs with shaking.

The final culture should contain 2 to $6\times10^6$ cells/ml. This is achieved by diluting using PB to $5*10^5$ cell/ml.

In-Vitro Susceptibility Testing

Caprylhydroxamic acid (0.5%) was prepared in DMSO, and 2-fold serially diluted in growth medium to prepare in a range of 5000-78 ppm. 20 μl of the serially dilutions were added into each column of the 96-well plate (corning-3788).

Testing Norbraylin compound (stock: 20 mg/ml in DMSO) was 2-fold serially diluted in growth meidum to prepare in a range of 20000-20 ppm. 20 μl of the serially dilutions will be added to each row of the 96—working plate (corning-3788), to create the binary combinations with caprylhydroxamic acid.

The final cell density in the testing plate is around $5*10^4$ cell/ml, and the final concentration of actives in each well of the 96-wel plate were shown below:

---
Norbraylin 2000, 1000, 500, 250, 125, 62.5, 31.25, 15.63, 7.8, 3.9, 2.0, 0 ppm
Caprylhydroxamic acid: 500, 250, 125, 62.5, 31.25, 15.63, 7.8, 0 ppm

---

For *M. furfur*, after 2-days incubation, OD600 (end) will be read. Then alamar blue (10%) was added and incubated for 8 hours. Color change from blue to red was recorded and fluorescence (530EX nm/590EM nm) was read.

It was observed that there was synergistic effect of caprylhydroxamic acid with norbraylin against *M. furfur* (Table 2).

TABLE 2

Effect of caprylhydroxamic acid and norbravlin against *M. furfur*

| Example | Combination | XFIC |
|---|---|---|
| 2 | Caprylhydroxamic acid + Norbraylin | 0.56 |

The observation tabulated in Tables 2 indicates that norbraylin interacts synergistically with caprylhydroxamic acid (the antimicrobial active according to the present invention).

All the experiments disclosed hereinabove were conducted under in vitro conditions to ascertain whether the combination of a specified antimicrobial active—piroctone olamine and norbraylin was synergistic, additive or antagonistic vis-a-vis their individual activity against the concerned microbe. As far as the experiments were concerned, the concentrations of the ingredients were chosen to fall within the allowable limits permitted by the concerned tests and in which it was possible to record the technical effects. Therefore, the concentrations at which the tests were conducted might not appear to fall within the range in which such ingredients are generally used in cosmetic compositions (usually in wt %).

The compositions of the invention may be formulated as an emulsion or a gel with other usual ingredients which may affect the concentration of the desired actives in the oil phase and in the water phase. Such compositions might also have a different set of physical and hydrodynamic properties like partition coefficients, diffusional rates, convective transport rates and rheological properties. Therefore, it is expected that the concentrations to be used when formulated as a composition could be different from that at the cellular levels at which the experiments were carried out and usually the in-use concentrations are orders of magnitude higher.

The invention claimed is:

1. A topical composition comprising:
   (i) an antimicrobial active which is at least one of piroctone, caprylhydroxamic acid, benzohydroxamic acid, or piroctone olamine; and
   (ii) norbraylin;
      wherein a weight ratio of an amount of the norbraylin to that of the antimicrobial active is from 1:10 to 100:1.

2. The composition as claimed in claim 1, wherein the composition comprises at least one of an extract of Zanthoxylum nitidum, extract of Toddalia asiatica, extract of Cedrelopsis grevei, or combinations thereof, wherein the at least one extract comprises said norbraylin.

3. The composition as claimed in claim 1, wherein said antimicrobial active is at least one of caprylhydroxamic acid or piroctone olamine.

4. The composition as claimed in claim 1, wherein an amount of said norbraylin is 0.01 to 10 wt %.

5. The composition as claimed in claim 1, wherein an amount of said antimicrobial active is 0.01 to 10 wt %.

6. The composition as claimed in claim 1, wherein the composition further comprises a cosmetically acceptable carrier comprising water.

7. The composition as claimed in claim 6, wherein the carrier further comprises a surfactant.

8. The composition as claimed in claim 1, wherein the composition is a wash-off or leave-on hair care composition.

9. The composition as claimed in claim 1 for use in providing antimicrobial benefit on a topical surface of a human or animal body.

10. The composition as claimed in claim 9 for use against at least some *Malassezia spp* on a topical surface of a human or animal body.

11. A topical composition comprising:
    (i) an antimicrobial active which is at least one of piroctone, caprylhydroxamic acid, benzohydroxamic acid, or piroctone olamine; and
    (ii) norbraylin;
       wherein an amount of said norbraylin is 0.01 to 10 wt %.

12. The composition as claimed in claim 11, wherein the composition comprises at least one of an extract of Zanthoxylum nitidum, extract of Toddalia asiatica, extract of Cedrelopsis grevei, or combinations thereof, wherein the at least one extract comprises said norbraylin.

13. The composition as claimed in claim 11, wherein said antimicrobial active is at least one of caprylhydroxamic acid or piroctone olamine.

14. The composition as claimed in claim 11, wherein an amount of said antimicrobial active is 0.01 to 10 wt %.

15. The composition as claimed in claim 11, wherein the composition further comprises a cosmetically acceptable carrier comprising water.

16. The composition as claimed in claim 11, wherein the carrier further comprises a surfactant.

17. The composition as claimed in claim 11, wherein the composition is a wash-off or leave-on hair care composition.

18. The composition as claimed in claim 11 for use in providing antimicrobial benefit on a topical surface of a human or animal body.

\* \* \* \* \*